United States Patent [19]
Yoshida et al.

[11] 3,998,593
[45] Dec. 21, 1976

[54] MEMBRANE BLOOD OXYGENATOR

[75] Inventors: Fumitake Yoshida; Shigeo Kato, both of Kyoto, Japan

[73] Assignee: Seisan Kaihatsu Kagaku Kenkyusho, Kyoto, Japan

[22] Filed: Feb. 11, 1976

[21] Appl. No.: 657,407

Related U.S. Application Data

[63] Continuation-in-part of Ser. No. 485,151, July 1, 1974, abandoned.

[30] Foreign Application Priority Data

July 2, 1973 Japan .............................. 48-75134
May 10, 1974 Japan .............................. 49-52553

[52] U.S. Cl. ..................... 23/258.5 MH; 55/158; 128/DIG. 3; 195/1.8
[51] Int. Cl.² .................................................. A61M 1/03
[58] Field of Search ............... 23/258.5, 258.5 MH; 210/321, 321 B; 128/DIG. 3; 55/158; 195/1.8

[56] References Cited
UNITED STATES PATENTS

| | | | |
|---|---|---|---|
| 3,034,505 | 5/1962 | Sobol | 23/258.5 M |
| 3,060,934 | 10/1962 | Claff et al. | 23/258.5 M |
| 3,266,629 | 8/1966 | Megibow | 210/321 B |
| 3,332,746 | 7/1967 | Claff et al. | 23/258.5 MH |
| 3,413,095 | 11/1968 | Bramson | 23/258.5 M |
| 3,459,310 | 8/1969 | Edwards | 23/258.5 M X |
| 3,484,211 | 12/1969 | Mon et al. | 23/258.5 MH |
| 3,503,850 | 3/1970 | Dibelius | 23/258.5 M X |
| 3,547,271 | 12/1970 | Edwards | 23/258.5 M X |
| 3,567,028 | 3/1971 | Nose | 23/258.5 M X |
| 3,612,281 | 10/1971 | Leonard | 23/258.5 M X |
| 3,834,544 | 9/1974 | Tyson et al. | 23/258.5 MH X |

OTHER PUBLICATIONS

Esmond et al., "Profound Hypothermia . . . Heat Exchanger of High Efficiency," J. Thoracic & Cardiovasc. Surgery, vol. 42, No. 5, 11/61, pp. 563-574.

*Primary Examiner*—Barry S. Richman
*Attorney, Agent, or Firm*—Mason, Fenwick & Lawrence

[57] ABSTRACT

A membrane blood oxygenator-blood heat exchanger combination including a gas exchange section of multi-layer structure having alternate layers of rectangular polymer membranes and rectangular mesh spacers forming alternate gas channels and gas exchange blood channels between the membranes, said gas and blood channels being generally perpendicular to each other; a heat exchange section having a multi-layer structure having alternate layers of metal sheets and rectangular mesh spacers forming alternate heat exchange blood channels and water channels, said blood and water channels being perpendicular to each other, said heat exchange blood channels being an extension of the gas exchange blood channels and having equal blood flow sectional area to said gas exchange blood channels.

4 Claims, 5 Drawing Figures

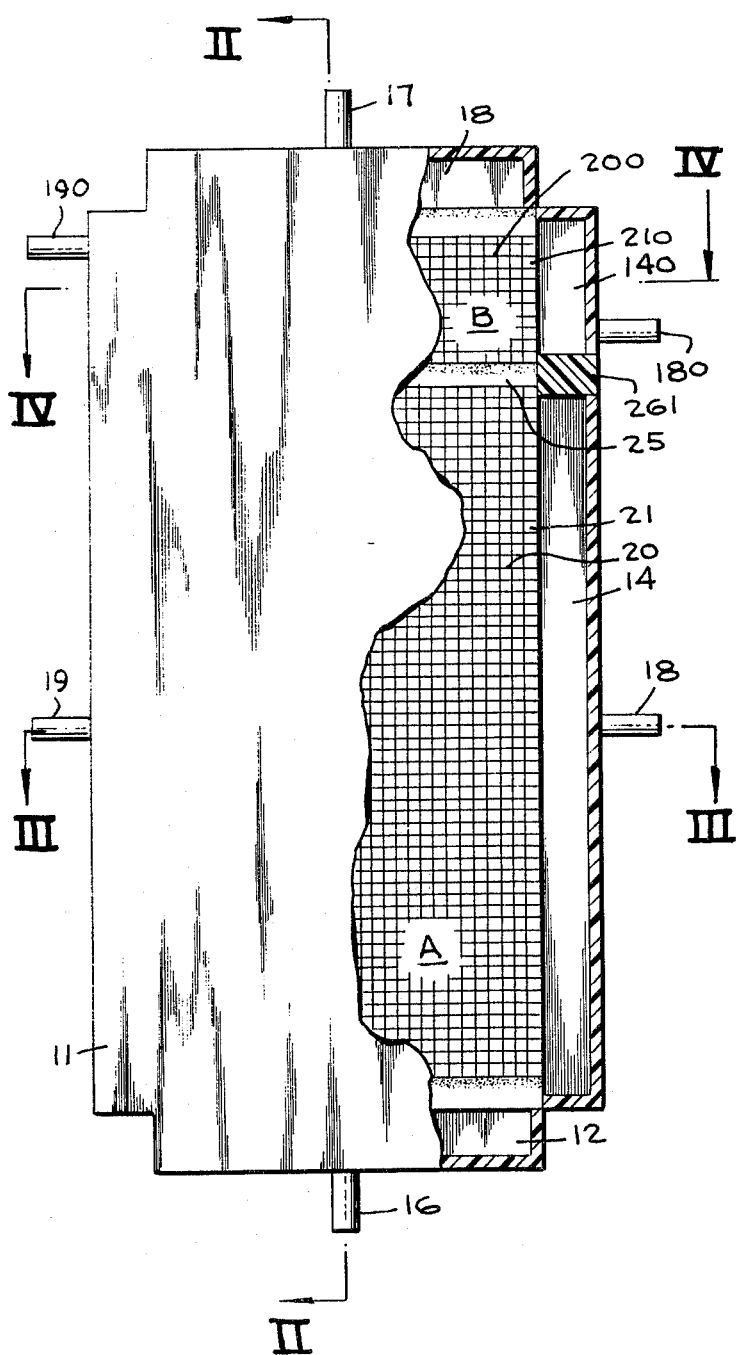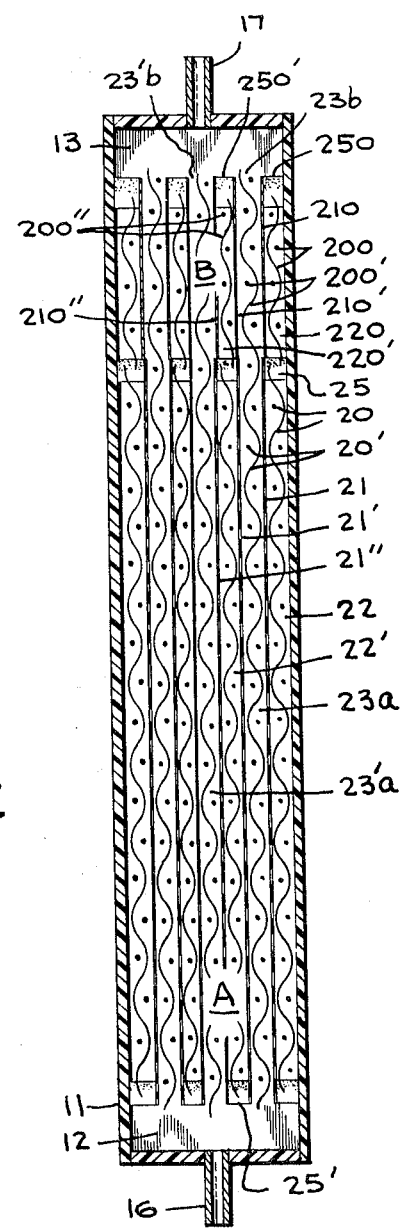

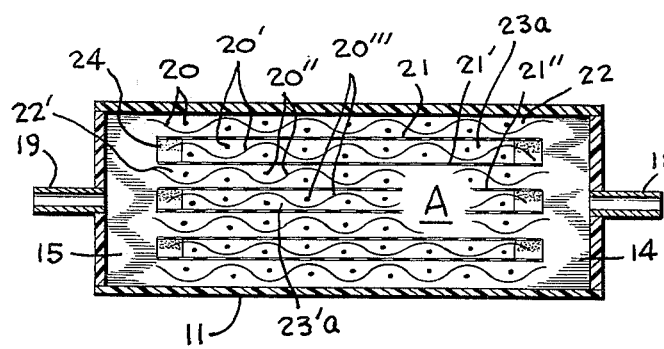
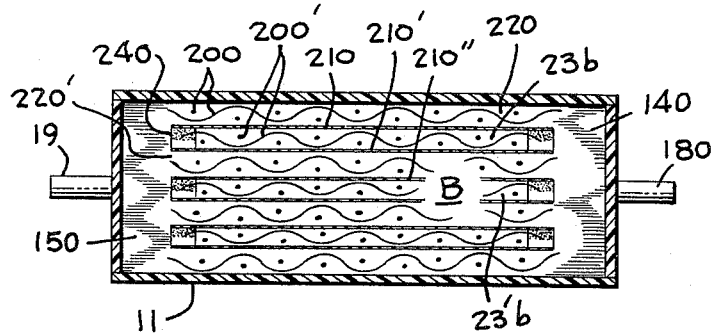
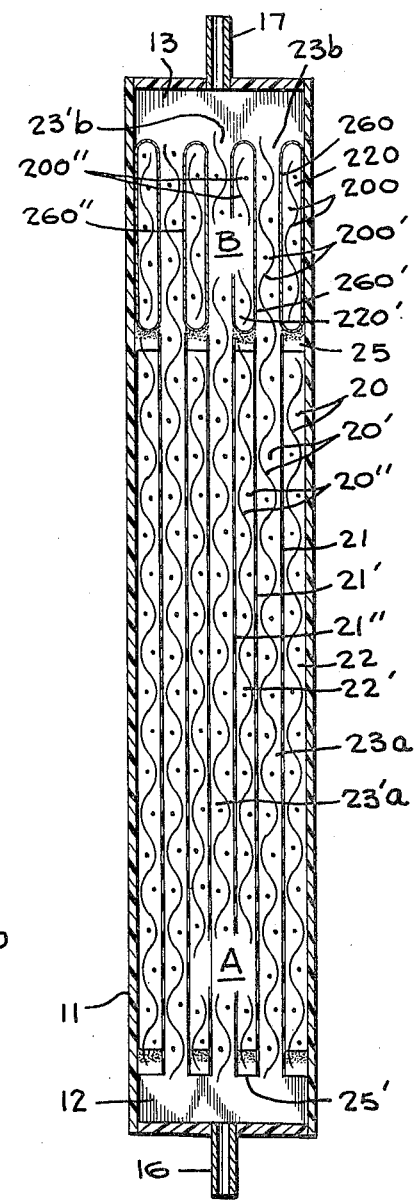

MEMBRANE BLOOD OXYGENATOR

This application is a continuation-in-part of Ser. No. 485,151, filed on July 1, 1974 and now abandoned.

BACKGROUND OF THE INVENTION

The present invention relates to a blood oxygenator (artificial lung) and more specifically relates to a membrane blood oxygenator having a multi-layer structure.

Blood oxygenators are used during heart surgery to temporarily perform the function of lungs. There are several types of blood oxygenators, such as the bubble-type, the rotating disc-type, and the membrane-type. The membrane-type, in which oxygen is absorbed into and carbon dioxide is desorbed from blood through membranes made of polymers such as silicone rubber, is considered to be superior to other types because there is less damage to blood components and hence less detrimental physiological effects.

A few of the representative types of membrane blood oxygenators and a similar device known before completion of the present invention will be briefly described. The Lande-Edwards disposable membrane oxygenator (U.S. Pat. Nos. 3,540,595; 3,541,595; 3,547,271) comprises a rectangular stack of grooved plastic support plates and pairs of silicone rubber membranes sandwiched between the plates. Blood flows between the membranes, and gas flows between the membranes and the plates through the grooves. It is said that a lung of this type having a membrane area as large as 5 sq. m. is required during heart surgery of an adult.

The parallel flow hemodialyzer, i.e. artificial kidney, of U.S. Pat. No. 3,565,258 uses a stack of flat cellophane tubes and mesh spacers. Dialysate liquid flows through the tubes, and blood flows outside the tubes. A device of this type cannot be used as a blood oxygenator, since the blood channels will collapse unless the gas space inside the tubes is kept at a lower pressure than the blood side.

During heart surgery with extracorporeal circulation, the blood temperature generally drops below the body temperature as blood circulates through the extracorporeal circuit thereby exposing the blood to the room temperature, which is below the body temperature. Thus it is often necessary to raise the temperature of blood before it returns to the body. On the other hand, when a heart surgery with hypothermia is performed, it is necessary to cool the blood. In either case, the blood temperature is controlled using a heat exchanger in which blood is warmed with hot water or cooled with cool water. The disposable membrane oxygenators described above are often used along with an independent heat exchanger. Since such a heat exchanger is not disposable, it must be cleaned and sterilized after each use. Although there are few disposable bubble oxygenators with built-in heat exchangers, no disposable membrane oxygenators with built-in heat exchangers are available on the market at present.

It is the primary object of the present invention to provide a new and improved membrane blood oxygenator.

It is an additional object of the present invention to provide an integral membrane blood oxygenator-blood heat exchanger in which damage to the blood such as hemolysis and thrombogenesis is reduced by minimizing changes in velocity and direction of blood flow through the device.

Another object of this invention is to provide a compact, disposable membrane blood oxygenator of simple construction which provides efficient gas exchange and temperature control.

These and other objects of the present invention have been attained by a membrane blood oxygenator comprising a gas exchange section of multi-layer construction including alternate layers of rectangular polymer membranes and rectangular mesh spacers forming alternate gas and blood channels between said membranes, said gas channels and said blood channels being perpendicular to each other and a heat exchange section of multilayer structure including alternate layers of metal sheets and rectangular mesh spacers forming alternate blood channels and water channels, said blood channels and said water channels being perpendicular to each other. The heat exchange blood channels are extensions of the gas exchange blood channels with the blood flow sectional area of both blood channels being equal.

BRIEF DESCRIPTION OF THE DRAWINGS

FIG. 1 is a fragmentary elevation of one embodiment of a device incorporating this invention;

FIG. 2 is a vertical sectional view taken along line II—II of FIG. 1;

FIG. 3 is a horizontal sectional view taken along line III—III of FIG. 1;

FIG. 4 is a horizontal sectional view taken along line IV—IV of FIG. 1; and

FIG. 5 is a vertical sectional view of an alternate embodiment of this invention.

DETAILED DESCRIPTION OF THE PREFERRED EMBODIMENTS

Referring to FIG. 1 which is a fragmentary elevational view of an embodiment of the device of this invention, A is the gas exchange section of multi-layer construction including alternate layers of rectangular polymer membranes 21 and rectangular mesh spacers 20 forming alternate gas and blood channels, said gas and blood channels being perpendicular to each other and said gas exchange section being contained in the casing 11. The blood inlet pipe 16 leads to the blood inlet chamber 12. The blood outlet chamber 13 leads to the blood outlet pipe 17. The gas inlet pipe 18 leads to the gas inlet chamber 14. In symmetry with the gas inlet chamber 14, there is a gas outlet chamber 15, shown in FIG. 3, leading to the gas outlet pipe 19.

Blood enters through the blood inlet pipe 16 and the blood inlet chamber 12, flows through the gas exchange section A, where gas exchange between blood and gas is performed, and then enters the heat exchange section B, which is disposed in a common casing 11 along with the gas exchange section A and is a multi-layer structure including alternate layers of rectangular metal sheets and rectangular mesh spacers forming alternate blood and water channels, said blood and water channels being perpendicular to each other. On top of the heat exchange section B, there is the blood outlet chamber 13 connected to each of the blood channels of the heat exchange section B and leading to the blood outlet pipe 17. Temperature-controlled water, used to warm or cool blood, enters through the water inlet pipe 180 and the water inlet chamber 140 to the water channels of the heat exchange section B, and leaves through the water outlet chamber 150, shown in FIG. 4, and the water outlet pipe 190. Gas, mainly oxygen, enters through the gas inlet pipe 18 and the gas inlet chamber 14, flows through the gas channels of the gas exchange section A, and leaves through the gas outlet chamber 15, shown in FIG. 3, and the gas outlet pipe 19. The sealing wall 261 is installed between the gas inlet chamber 14 and the water inlet chamber 140. There is a similar sealing wall between the gas outlet chamber 15 and the water outlet chamber 150 which is not shown in FIG. 1.

FIG. 2 shows a vertical sectional view taken on line II—II of FIG. 1 with the section being parallel to the direction of blood flow. FIG. 3 and 4 are horizontal sectional views with both sections being perpendicular to the direction of blood flow.

Both FIG. 2 and FIG. 3 show the details of the structure of the gas exchange section A. In both figures, the rectangular mesh spacers are identified as 20, 20' and 20'' and the rectangular polymer membranes are identified as 21, 21' and 21''. These mesh spacers and membranes are alternately stacked to form the gas channels 22, 22', and the blood channels 23a, 23a', with said gas and blood channels being perpendicular to each other. Each pair of polymer membranes forming a chanel, together with the mesh spacer in the channel, are sealed with an adhesive at both edges of the channel with the edges being parallel to the direction of fluid flow in the channel. For example, the polymer membranes 21' and 21'' forming the gas channel 22' are sealed with the adhesive 25' together with the mesh spacer 20''. The length of the mesh spacer 20' in the blood channel 23a is not shorter than the length of the blood channel in the direction of blood flow.

FIG. 3 shows the polymer membranes 21 and 21' with the mesh spacer 20' sealed with an adhesive 24. The mesh spacers 20, 20'' in the gas channels 22, 22' are not shorter than the length of the gas channels in the direction of gas flow.

Details of the structure of the gas exchange section A can be well understood from FIGS. 2 and 3. In the explanation of the gas and blood channels, the gas channel 22' and the blood channel 23a were taken merely as examples. The other gas and blood channels are of similar structure except for the gas channels facing the inner surfaces of the casing. The polymer membrane 21 and the inner surface of the casing 11 are sealed with an adhesive 25 together with the mesh spacer 20 at the edges of the gas channel parallel to the direction of gas flow. The other gas channel facing the other inner surface of the casing is of the same structure. The number of the gas and blood channels can be increased as desired by increasing the number of polymer membranes and mesh spacers. The gas inlet chamber 14 and the gas outlet chamber 15 are connected to both ends of each of the gas channels 22, 22'.

Referring to FIGS. 2 and 4, the heat exchange section B is a multi-layer structure including alternate layers of rectangular metal sheets 210, 210' and rectangular mesh spacers 200, 200' which alternately form the blood channels 23b, 23'b and the water channels 220, 220', the blood channels and water channels being perpendicular to each other. Each pair of metal sheets forming a fluid channel together with the mesh spacer in the channels, are sealed by an adhesive at the edges parallel to the flow of fluid in the channel. FIG. 2 shows how the rectangular metal sheets 210' and 210'' forming the water channel 220', together with the mesh spacer 200'' in the channel, are sealed by an adhesive 250' at the edges parallel to the direction of water flow.

The mesh spacers 200' in the heat exchange blood channel 23b can be extensions of the mesh spacers 20' in the gas exchange blood channels 23a or separate ones.

FIG. 4 shows the rectangular metal sheets 210 and 210' forming the blood channel 23b, along with the mesh spacer 200', sealed with an adhesive 240 at the edges paralel to the direction of blood flow.

In the heat exchange section, it is not permissible for the mesh spacers in the fluid channels to be shorter than the length of the channel in the flow direction, if the metal sheets forming the channels are sufficiently stiff so that the channels do not collapse due to fluid pressure.

FIGS. 2 and 4 show that the water channel 220 facing the inner wall of the casing 11 is slightly different in construction from the other water channels. It is formed by sealing the metal sheet 210 to the casing wall 11 together with the mesh spacer 200. It is desirable to use the channels facing the casing wall as water channels to increase the efficiency of the device.

In FIG. 4, 140 and 150 are the water inlet and outlet chambers, respectively, which are connected to each of the water channels 220, 220'.

Since the mesh spacer in each of the blood or gas channels is not shorter than the length of the channel in the flow direction and extends over the whole length, it produces turbulence in the blood or gas stream in the channels, thus increasing the mass transfer coefficient and reducing the membrane area required. The mesh spacer prevents the channels from collapsing due to fluid pressure and equalizes the rate of fluid flow into each of the fluid channels while making the velocity distribution uniform within a fluid channel. Use of mesh spacers, along with the fact that the gas and blood flows are perpendicular to each other, prevents formation of dead spaces where fluid is stagnant and hence local efficiency of gas exchange would be low. Where blood flow is stagnant, the formation of dangerous thrombus is also possible.

Presence of mesh spacers in the blood and water channels in the heat exchange section produces turbulence in the fluids in the channels, thus increasing the heat transfer coefficient. Furthermore, there exist no dead spaces where fluids are stagnant. Thus, the heat transfer area may be reduced compared to devices without mesh spacers. Additionally, the mesh spacers equalize the rate of fluid flow into each fluid channel and make the fluid velocity distribution uniform within a fluid channel.

Since the heat exchange blood channels are extensions of the gas exchange blood channels and both blood channels have equal blood flow sectional area, there is no change in velocity and direction of blood flow through the gas exchange and heat exchange sections. Thus, damage to blood such as hemolysis and thrombosis is minimized.

There are many possible alternate embodiments of this invention. FIG. 5 is a vertical sectional view of another alternate embodiment of the device of this invention, in which the heat exchange section consists of alternatively arranged stacks of rectangular mesh spacers 200 and 200', and flattened metal tubes 260 and 260' with said flattened tubes or envelopes containing mesh spacers 200 and 200'' and forming water channel 220 and 220'. A flattened metal tube is used in place of a pair of rectangular metal sheets joined and sealed at two edges parallel to the water flow. The space outside and between flattened tubes form heat exchange blood channels 23b and 23'b with the blood channels being sealed at respective ends parallel to blood flow and perpendicular to water flow. The working principle and the fluid flow patterns with the embodiment shown in FIG. 5 are exactly the same as with the embodiment, of which the heat exchange section is shown in FIGS. 2 and 4. The heat exchange section of the embodiment shown in FIG. 5 has advantages over the embodiment shown in FIGS. 1 to 4 in that it is easier to construct and there is less risk of leakage of water into blood, in case water pressure is higher than blood pressure. The mesh spacers in the water channels could be dispensed with, if so desired.

EXAMPLE

This example was performed with a membrane blood oxygenator-blood heat exchanger combination of the construction shown in FIGS. 1, 2, 3 and 4. The membrane area is 1.0 sq. meter.

The gas exchange section was of multi-layer construction with the following major dimensions:

Membrane (silicone rubber): 100 microns thick, 13.5 cm long (in the blood flow direction), 15 cm wide; mesh spacers (polyester resin for blood channels, and Saran for gas channels): about 0.5 mm thick, 13.5 cm long (in the blood flow direction), 15 cm wide; number of blood channels: 25, number of gas channels: 26.

The heat exchange section was of multi-layer construction with the following major dimensions:

Aluminum metal sheets: about 0.2 mm thick, 6 cm long (in the blood flow direction), 15 cm wide; mesh spacers (polyester resin for blood channels and Saran for water channels): about 0.5 mm thick, 6 cm long (in the blood flow direction), 15 cm wide; number of blood channels: 25; number of water channels: 26.

During the experiments, the percentage oxygen saturation of the blood at the inlet was 80 percent. The blood flow rate was 4.0 liters per minute. Blood was warmed from 30.0° C to 35.3° C by hot water, which was temperature-controlled at 40.0° C. The experimental results obtained are given in TABLE I. The experimental data shown in TABLE I indicate that the device of the invention can be used efficiently for heart surgery.

TABLE I

| | |
|---|---|
| membrane area, sq. m. | 1.0 |
| heat transfer area, sq. m. | 0.44 |
| oxygen absorption, c.c./min. | 85 |
| outlet blood temp., ° C | 35.3 |

It will be understood that the drawing and specific description have been given for purpose of illustration only and that variations and modifications can be made therein without departing from the spirit and scope of the appended claims.

We claim:

1. A membrane blood oxygenator-blood heat exchanger combination comprising: a gas exchange section having a multi-layer structure consisting of alternate layers of rectangular polymer membranes and rectangular mesh spacers forming alternate gas channels and gas exchange blood channels between said membranes, said gas channels being sealed from said blood channels, said gas channels and said blood channels being perpendicular to each other with respect to the directions of gas flow and blood flow, a heat exchange section having a multi-layer structure consisting of alternate layers of metal sheets and rectangular mesh spacers forming alternate heat exchange blood channels and water channels between said metal sheets, said heat exchange blood channels and said water channels being perpendicular to each other with respect to the directions of blood flow and water flow, said heat exchange blood channels being sealed from said water channels, each of said heat exchange blood channels being aligned with and forming an extension of a respective each of said gas exchange blood channels and having a blood flow sectional area equal to the blood flow sectional area of the gas exchange section; a gas inlet chamber and a gas outlet chamber connected to respective ends of each of said gas channels of said gas exchange section; a water inlet chamber and a water outlet chamber connected to respective ends of each of said water channels of said heat exchange section; a blood inlet chamber connected to one end of each of said blood channels of said gas exchange section; a blood outlet chamber connected to one end of each of said heat exchange blood channels of said heating exchange section; and a casing which contains said gas exchange section, said heat exchange section, said gas inlet chamber and said outlet chamber, said water inlet chamber and outlet chamber, and said blood inlet chamber and outlet chamber, thereby providing an integral blood oxygenator and blood heat exchanger in which the blood flows at a constant velocity without changing direction and in series through the oxygenator and heat exchanger with gas on both sides of the blood channels as the blood flows through the gas exchange section and water on both sides of the blood channels as the blood flows through the heat exchange section.

2. The membrane blood oxygenator-blood heat exchanger combination of claim 1 wherein the heat exchange section consists of alternate layers of rectangular metal sheets and rectangula mesh spacers forming alternate heat exchanger blood channels and water channels between said metal sheets, said blood channels being sealed at respective ends parallel to blood flow, and said water channels being sealed at respective ends perpendicular to blood flow.

3. A membrane blood oxygenator-blood heat exchanger combination comprising: a gas exchange section having a multi-layer structure consisting of alternate layers of rectangular polymer membranes and rectangular mesh spacers forming alternate gas channels and gas exchange blood channels between said membranes, said gas channels being sealed from said blood channels, said gas channels and said blood channels being perpendicular to each other with respect to the direction of gas flow and blood flow, a heat exchange section having a multi-layer structure consisting of alternate layers of rectangular mesh spacers and flattened metal tubes, said flattened tubes forming water channels, and the space outside and between flattened tubes forming heat exchange blood channels, said heat exchange blood channels and said water channels being perpendicular to each other with respect to the directions of blood flow and water flow, said heat exchange blood channels being sealed from said water channels, each of said heat exchange blood channels being aligned with and forming an extension of a respective each of said gas exchange blood channels and having a blood flow sectional area equal to the blood flow sectional area of the gas exchange section; a gas inlet chamber and a gas outlet chamber connected to respective ends of each of said gas channels of said gas exchange section; a water inlet chamber and water outlet chamber connected to respective ends of each of said water channels of said heat exchange section; a blood inlet chamber connected to one end of each of said blood channels of said gas exchange section; a blood outlet chamber connected to one end of each of said heat exchange blood channels of said heat exchange section; and a casing which contains said gas exchange section, said heat exchange section, said gas inlet chamber and said outlet chamber, said water inlet chamber and outlet chamber, and said blood inlet chamber and outlet chamber, thereby providing an integral blood oxygenator and blood heat exchanger in which the blood flows at a constant velocity without changing direction and in series through the oxygenator and heat exchanger with gas on both sides of the blood channels as the blood flows through the gas exchange section and water on both sides of the blood channels as the blood flows through the heat exchange section.

4. A membrane blood oxygenator-blood heat exchanger combination of claim 3, wherein said flattened tubes forming water channels contain mesh spacers.

* * * * *